United States Patent [19]

Matthews et al.

[11] Patent Number: 4,929,770

[45] Date of Patent: May 29, 1990

[54] ALUMINUM PHENOXIDE CATALYST REMOVAL

[75] Inventors: Charles W. Matthews, Orangeburg, S.C.; Eric S. Batman, Belleville, Ill.; Jeffrey F. King, Orangeburg, S.C.

[73] Assignee: Ethyl Corporation, Richmond, Va.

[21] Appl. No.: 320,540

[22] Filed: Mar. 8, 1989

[51] Int. Cl.$^5$ .................. C07C 37/70; C07C 37/74
[52] U.S. Cl. ...................................... 568/756; 568/749
[58] Field of Search ............... 568/756, 749, 789, 794

[56] References Cited

U.S. PATENT DOCUMENTS

| | | | |
|---|---|---|---|
| 2,831,898 | 4/1958 | Eckes et al. | 568/789 |
| 3,652,685 | 3/1972 | Geddes | 568/756 |
| 3,766,276 | 10/1973 | Goddard | 568/774 |
| 3,939,215 | 2/1976 | Goddard | 568/756 |
| 3,970,708 | 7/1976 | Katsumoto | 568/756 |
| 4,232,176 | 11/1980 | Adigamov et al. | 568/756 |

*Primary Examiner*—Werren B. Lone
*Attorney, Agent, or Firm*—Joseph D. Odenweller

[57] ABSTRACT

Aluminum phenoxide catalyst is removed from a phenolic alkylation mixture by adding 15–30 moles of water per mole of aluminum phenoxide to the alkylation mixture and holding at about 30°–100° C. for 10–60 minutes to form solids and heating the wet mixture to 120°–160° C. and holding at that temperature until filterable particulates form. The particulates can be readily filtered to obtain a substantially aluminum-free filtrate.

5 Claims, No Drawings

ALUMINUM PHENOXIDE CATALYST REMOVAL

BACKGROUND

Since the pioneering discovery of Ecke et al., U. S. Pat. No. 2,831,898, it has been possible to alkylate phenols selectively in the ortho position by reaction of a phenol having an open ortho position with an olefin, preferably a di-substituted (i.e. secondary) or tri-substituted (i.e. tert-olefin), in the presence of an aluminum phenoxide catalyst (i.e. an aluminum compound having at least one phenoxide or alkylphenoxide group bonded to aluminum). Following the alkylation it is necessary to deactivate the catalyst to prevent dealkylation and isomerization. Since the products are conventionally recovered by distillation, it is also necessary to remove the aluminum compounds to avoid pluggage of the distillation column. In a conventional process this can be accomplished by washing the completed alkylation mixture with a dilute aqueous acid solution such as dilute $H_3PO_4$, HCl or acetic acid. This results in a spent aqueous wash solution which contains phenol and/or phenolic compounds and aluminum salts which present a formidable disposal problem.

Attempts have been made to circumvent the wash step by precipitating the aluminum phenoxide in a manner that permits removal of the aluminum containing residue by filtration. This is a difficult goal to achieve because aluminum compounds under neutral or basic conditions have a propensity to form gels which quickly plug any filter medium.

Geddes, U.S. Pat. No. 3,652,685, describe a method of catalyst removal in which a minimal amount of only 3–6 moles of water per mole of aluminum phenoxide are added to the alkylation mixture followed by filtration at 90°–160° C. in a pressure filter.

Katsumoto, U.S. Pat. No. 3,970,708, describe a modification of the Geddes process in which a neutral inorganic salt, e.g. sodium sulfate, is added to the reaction mixture along with the water to improve filtration rate.

Adigamov et al., U.S. Pat. No. 4,232,176, describe another method for removing the aluminum-containing catalyst in which a 3–20 molar excess of water based on aluminum is added to the reaction mixture which is heated to the critical range of 165°–250° C. under vacuum to form meta-aluminate. This is said to be readily removed by filtration.

SUMMARY

It has now been discovered that the aluminum-containing catalyst in a phenol alkylation mixture can be readily removed without the necessity of limited water addition or heating above 165° C. by adding at least 15 moles of water per mole of aluminum-containing catalyst and heating the wet mixture at 120°–160° C. Heating to a higher temperature than 160° C. is not detrimental but is unnecessary. The solids formed can be removed by filtration.

DESCRIPTION OF THE PREFERRED EMBODIMENTS

A preferred embodiment of the invention is a method of removing aluminum phenoxide catalyst from a phenol alkylation mixture containing 15–450 moles of phenolic compounds per mole of aluminum phenoxide said method comprising:

(A) adding about 15–30 moles of water per mole aluminum phenoxide to the phenol alkylation mixture to obtain a wet alkylation mixture containing fluffy unfilterable solids, (B) maintaining the wet alkylation mixture at a temperature of 120°–160° C. while distilling out water until filterable solid particulates form and, (C) removing said solid particulates from said alkylation mixture.

The phenol alkylation mixture results from the alkylation of a phenol with an olefin using an aluminum phenoxide catalyst. Such aluminum phenoxide catalysts have at least one phenoxy or substituted phenoxy group bonded to aluminum. These aluminum triaryloxides such as aluminum triphenoxide, aluminum tri-(2-tert-butylphenoxide), aluminum tri-(4-methyl phenoxide) and the like. In like manner aryloxy aluminum halides or hydroxides can be used as catalysts such as diphenoxy aluminum chloride, phenoxy aluminum chloride, diphenoxy aluminum hydroxide, phenoxy aluminum dibromide and the like.

The amount of aluminum phenoxide catalyst can vary over a wide range. This is expressed in terms of moles of phenol per mole of aluminum catalyst. This ratio can range from 10:1 to about 500:1 but usually is in the range of 15:1 to 450:1.

The phenolic compounds can be any that have an unsubstituted ortho position. This includes phenol, o-cresol, p-cresol, p-ethylphenol, α-naphthol and the like. The most important phenolic compound is phenol itself or phenol mixtures containing alkylphenols recycled from a prior alkylation such as 2-tert-butylphenol, 2,4-di-tert-butylphenol, 4-tert-butylphenol and the like.

The preferred olefins are vinyl olefins R—CH=CH$_2$, vinylidene olefins R—CH(=CH$_2$)—R, di-substituted olefins R—CH=CH—R, also called secondary olefins and tri-substituted olefins RRC=CHR, also called tert-olefins. Examples of these are propylene, 1-butene, 2-butene, 1-hexene, 2-ethyl-1-hexene, isobutene, isopentene, cyclopentene, cyclohexene, styrene, α-methylstyrene and the like.

The mole ratio of olefin to phenolic compound can range from about 1:1 to 3:1. When di-ortho-alkylation is desired the preferred ratio is about 2.2:1.

The alkylation temperature ranges from about 80°–150° C. and preferably about 90°–125° C. Pressure varies with temperature but usually ranges at about 50–300 psig when using isobutylene.

When the alkylation reaction is complete the reaction is cooled and vented. It is then necessary to remove the aluminum phenoxide catalyst prior to distillation to recover product. In a conventional process this is accomplished using an aqueous acid (e.g. $H_3PO_4$, HCl, acetic acid) wash. The wash fluid contains soluble aluminum salts and phenolic compounds both of which present a disposal problem.

Although other procedures have been disclosed for removing the aluminum catalyst as a solid, filterable product, tests have shown that greatly superior results can be obtained following the process of this invention.

In a first stage, 15–30 moles of water per mole of aluminum catalyst are added to and mixed with the alkylation mixture. A more preferred amount of water is about 15–25 moles per mole of aluminum and most preferably about 20–25 moles per mole of aluminum compound. At this stage a fluffy non-filterable solid forms.

The wet mixture is then stirred and heated to 120°–160° C. Stirring is continued in this temperature range while permitting water to distill out until filterable solids form. The time for this to occur varies but is usually in the range of 0.5–4.0 hours, generally 0.5–3.0 hours. The particulates (10 micron average particle size) are easily removed by filtration.

In a more preferred embodiment, the wet alkylation mixture is held at 30°–100° C. for about 5–120 minutes before being heated to 120°–160° C. Still more preferably the wet mixture is held at 60°–90° C. for 10–60 minutes prior to heating to 120°–160° C. Fluffy non-filterable solids form at this stage.

A highly preferred embodiment of the invention is a process for removing aluminum phenoxide catalyst from a phenol alkylation mixture, said mixture comprising about 65–90 weight percent 2,6-di-tert-butyl phenol and containing 0.07–0.002 moles of an aluminum phenoxide per mole of phenolic component in said alkylation mixture, said process comprising:

(A) adding about 15–25 moles of water per mole of said aluminum phenoxide to said alkylation mixture to obtain a wet alkylation mixture,
(B) holding the wet alkylation mixture at a temperature of about 60°–90° C. for about 10–60 minutes to form fluffy unfilterable particulates,
(C) heating said wet alkylation mixture to about 120°–160° C. and holding at 120°–160° C. for 30–180 minutes while distilling out water to form filterable solid particulates,
(D) filtering said alkylation mixture to remove said particulate and recover a substantially aluminum-free filtrate.

The process has its greatest utility when used to remove catalyst from a phenol butylation reaction mixture in which the mole ratio of phenolic compound to aluminum phenoxide is about 100–450 to 1.0. Expressed another way this is 0.01–0.002 moles of aluminum catalyst per mole of phenolic compound.

The following example shows how the process can be carried out. All parts are by weight.

EXAMPLE

A phenol alkylation mixture was prepared from 177.5 parts of phenol, 1.06 parts triethyl aluminum (which reacted with the phenol to form aluminum phenoxide) and 232.81 parts of isobutylene. The alkylation was carried out at 115° C. and 190–220 psig except during the addition of the last 15.85 parts of isobutylene which was conducted at 70° C. The mixture was then stirred at 70° C. for 3 hours to complete the reaction. The reactor was vented to atmospheric pressure and, while still at 70° C., 3.67 parts of water were added. The wet mixture was stirred at 70° C. for 45 minutes and then heated to 150° C. while at atmospheric pressure and stirred at 150° C. for 45 minutes while allowing water to distill out. It was then cooled to 90° C. and filtered. The precipitate was granular and filtered rapidly using a 1 micron bag filter. The main product, 2,6-di-tert-butylphenol, was recovered by distillation.

We claim:

1. A method of removing aluminum phenoxide catalyst from a phenol alkylation mixture containing 15–450 moles of phenolic compound per mole of aluminum phenoxide, said method comprising:
   (A) adding about 15–30 moles of water per mole of aluminum phenoxide to the phenol alkylation mixture to obtain a wet alkylation mixture,
   (B) maintaining said wet alkylation mixture at about 30°–100° C. for about 5–120 minutes and then,
   (C) maintaining the wet alkylation mixture at a temperature of 120°–160° C. while distilling out water until filterable solid particulates form and,
   (D) removing said solid particulates from said alkylation mixture.

2. A process of claim 1 wherein said phenol alkylation mixture is formed by reacting phenol or a mixture of phenolic compounds containing mainly phenol and containing about 0.07–0.002 moles of an aluminum phenoxide per mole of phenol or phenolic compound, with isobutylene to form an alkylation mixture containing mainly 2,6-di-tert-butylphenol.

3. A process of claim 2 wherein said phenol alkylation mixture contains about 0.01–0.002 moles of an aluminum phenoxide per mole of phenol or phenolic compound.

4. A process for removing aluminum phenoxide catalyst from a phenol alkylation mixture, said mixture comprising about 65–90 weight percent 2,6-di-tert-butyl phenol and containing 0.07–0.002 moles of an aluminum phenoxide per mole of phenolic component in said alkylation mixture, said process comprising:
   (A) adding about 15–25 moles of water per mole of said aluminum phenoxide to said alkylation mixture to obtain a wet alkylation mixture,
   (B) holding the wet alkylation mixture at a temperature of about 60°–90° C. for about 10–60 minutes to form solids,
   (C) heating said wet alkylation mixture to about 120°–160° C. and holding at 120°–160° C. for 30–180 minutes while distilling out water to form a filterable solid particulate,
   (D) filtering said alkylation mixture to remove said particulate and recover a substantially aluminum-free filtrate.

5. A process of claim 4 wherein the alkylation mixture contains 0.01–0.002 moles of aluminum phenoxide per mole of phenolic component.

* * * * *